(12) United States Patent
Boesen et al.

(10) Patent No.: US 10,117,604 B2
(45) Date of Patent: Nov. 6, 2018

(54) 3D SOUND POSITIONING WITH DISTRIBUTED SENSORS

(71) Applicant: BRAGI GmbH, München (DE)

(72) Inventors: Peter Vincent Boesen, München (DE); Darko Dragicevic, München (DE)

(73) Assignee: BRAGI GmbH, München (DE)

( * ) Notice: Subject to any disclaimer, the term of this patent is extended or adjusted under 35 U.S.C. 154(b) by 0 days.

(21) Appl. No.: 15/799,623

(22) Filed: Oct. 31, 2017

(65) Prior Publication Data

US 2018/0116564 A1 May 3, 2018

Related U.S. Application Data

(60) Provisional application No. 62/416,587, filed on Nov. 2, 2016.

(51) Int. Cl.
| | |
|---|---|
| *H04R 5/02* | (2006.01) |
| *A61B 5/12* | (2006.01) |
| *G06F 3/01* | (2006.01) |
| *H04R 1/10* | (2006.01) |

(52) U.S. Cl.
CPC ............... *A61B 5/12* (2013.01); *G06F 3/017* (2013.01); *H04R 1/105* (2013.01); *H04R 1/1016* (2013.01); *H04R 1/1066* (2013.01); *H04R 1/1091* (2013.01); *H04R 2420/07* (2013.01)

(58) Field of Classification Search
CPC ......... A61B 5/12; G06F 3/017; H04R 1/1016; H04R 1/105; H04R 1/1066; H04R 1/1091; H04R 2420/07
See application file for complete search history.

(56) References Cited

U.S. PATENT DOCUMENTS

| | | | |
|---|---|---|---|
| 2,325,590 | A | 8/1943 | Carlisle et al. |
| 2,430,229 | A | 11/1947 | Kelsey |
| 3,047,089 | A | 7/1962 | Zwislocki |
| D208,784 | S | 10/1967 | Sanzone |

(Continued)

FOREIGN PATENT DOCUMENTS

| | | |
|---|---|---|
| CN | 204244472 U | 4/2015 |
| CN | 104683519 A | 6/2015 |

(Continued)

OTHER PUBLICATIONS

Wikipedia, "Wii Balance Board", "https://en.wikipedia.org/wiki/Wii_Balance_Board", 3 pages, (Jul. 20, 2017).

(Continued)

*Primary Examiner* — Andrew L Sniezek
(74) *Attorney, Agent, or Firm* — Goodhue, Coleman & Owens, P.C.

(57) ABSTRACT

A method of providing audiometric feedback from a network of distributed body sensors using one or more earpieces includes receiving signals from the network of distributed body sensors at the one or more wireless earpieces, processing the signals received at the one or more wireless earpieces to determine a location of individual body sensors within the network of distributed body sensors relative the one or more earpieces, and producing audiometric feedback at the one or more wireless earpieces at least partially based on the locations of the individual body sensors relative to the one or more earpieces.

20 Claims, 5 Drawing Sheets

(56) References Cited

U.S. PATENT DOCUMENTS

| | | |
|---|---|---|
| 3,586,794 A | 6/1971 | Michaelis |
| 3,934,100 A | 1/1976 | Harada |
| 3,983,336 A | 9/1976 | Malek et al. |
| 4,069,400 A | 1/1978 | Johanson et al. |
| 4,150,262 A | 4/1979 | Ono |
| 4,334,315 A | 6/1982 | Ono et al. |
| D266,271 S | 9/1982 | Johanson et al. |
| 4,375,016 A | 2/1983 | Harada |
| 4,588,867 A | 5/1986 | Konomi |
| 4,617,429 A | 10/1986 | Bellafiore |
| 4,654,883 A | 3/1987 | Iwata |
| 4,682,180 A | 7/1987 | Gans |
| 4,791,673 A | 12/1988 | Schreiber |
| 4,852,177 A | 7/1989 | Ambrose |
| 4,865,044 A | 9/1989 | Wallace et al. |
| 4,984,277 A | 1/1991 | Bisgaard et al. |
| 5,008,943 A | 4/1991 | Arndt et al. |
| 5,185,802 A | 2/1993 | Stanton |
| 5,191,602 A | 3/1993 | Regen et al. |
| 5,201,007 A | 4/1993 | Ward et al. |
| 5,201,008 A | 4/1993 | Arndt et al. |
| D340,286 S | 10/1993 | Seo |
| 5,280,524 A | 1/1994 | Norris |
| 5,295,193 A | 3/1994 | Ono |
| 5,298,692 A | 3/1994 | Ikeda et al. |
| 5,343,532 A | 8/1994 | Shugart |
| 5,347,584 A | 9/1994 | Narisawa |
| 5,363,444 A | 11/1994 | Norris |
| D367,113 S | 2/1996 | Weeks |
| 5,497,339 A | 3/1996 | Bernard |
| 5,606,621 A | 2/1997 | Reiter et al. |
| 5,613,222 A | 3/1997 | Guenther |
| 5,654,530 A | 8/1997 | Sauer et al. |
| 5,692,059 A | 11/1997 | Kruger |
| 5,721,783 A | 2/1998 | Anderson |
| 5,748,743 A | 5/1998 | Weeks |
| 5,749,072 A | 5/1998 | Mazurkiewicz et al. |
| 5,771,438 A | 6/1998 | Palermo et al. |
| D397,796 S | 9/1998 | Yabe et al. |
| 5,802,167 A | 9/1998 | Hong |
| D410,008 S | 5/1999 | Almqvist |
| 5,929,774 A | 7/1999 | Charlton |
| 5,933,506 A | 8/1999 | Aoki et al. |
| 5,949,896 A | 9/1999 | Nageno et al. |
| 5,987,146 A | 11/1999 | Pluvinage et al. |
| 6,021,207 A | 2/2000 | Puthuff et al. |
| 6,054,989 A | 4/2000 | Robertson et al. |
| 6,081,724 A | 6/2000 | Wilson |
| 6,084,526 A | 7/2000 | Blotky et al. |
| 6,094,492 A | 7/2000 | Boesen |
| 6,111,569 A | 8/2000 | Brusky et al. |
| 6,112,103 A | 8/2000 | Puthuff |
| 6,157,727 A | 12/2000 | Rueda |
| 6,167,039 A | 12/2000 | Karlsson et al. |
| 6,181,801 B1 | 1/2001 | Puthuff et al. |
| 6,208,372 B1 | 3/2001 | Barraclough |
| 6,230,029 B1 | 5/2001 | Yegiazaryan et al. |
| 6,275,789 B1 | 8/2001 | Moser et al. |
| 6,339,754 B1 | 1/2002 | Flanagan et al. |
| D455,835 S | 4/2002 | Anderson et al. |
| 6,408,081 B1 | 6/2002 | Boesen |
| 6,424,820 B1 | 7/2002 | Burdick et al. |
| D464,039 S | 10/2002 | Boesen |
| 6,470,893 B1 | 10/2002 | Boesen |
| D468,299 S | 1/2003 | Boesen |
| D468,300 S | 1/2003 | Boesen |
| 6,542,721 B2 | 4/2003 | Boesen |
| 6,560,468 B1 | 5/2003 | Boesen |
| 6,654,721 B2 | 11/2003 | Handelman |
| 6,664,713 B2 | 12/2003 | Boesen |
| 6,690,807 B1 | 2/2004 | Meyer |
| 6,694,180 B1 | 2/2004 | Boesen |
| 6,718,043 B1 | 4/2004 | Boesen |
| 6,738,485 B1 | 5/2004 | Boesen |
| 6,748,095 B1 | 6/2004 | Goss |
| 6,754,358 B1 | 6/2004 | Boesen et al. |
| 6,784,873 B1 | 8/2004 | Boesen et al. |
| 6,823,195 B1 | 11/2004 | Boesen |
| 6,852,084 B1 | 2/2005 | Boesen |
| 6,879,698 B2 | 4/2005 | Boesen |
| 6,892,082 B2 | 5/2005 | Boesen |
| 6,920,229 B2 | 7/2005 | Boesen |
| 6,952,483 B2 | 10/2005 | Boesen et al. |
| 6,987,986 B2 | 1/2006 | Boesen |
| 7,010,137 B1 | 3/2006 | Leedom et al. |
| 7,113,611 B2 | 9/2006 | Leedom et al. |
| D532,520 S | 11/2006 | Kampmeier et al. |
| 7,136,282 B1 | 11/2006 | Rebeske |
| 7,203,331 B2 | 4/2007 | Boesen |
| 7,209,569 B2 | 4/2007 | Boesen |
| 7,215,790 B2 | 5/2007 | Boesen et al. |
| D549,222 S | 8/2007 | Huang |
| D554,756 S | 11/2007 | Sjursen et al. |
| 7,403,629 B1 | 7/2008 | Aceti et al. |
| D579,006 S | 10/2008 | Kim et al. |
| 7,463,902 B2 | 12/2008 | Boesen |
| 7,508,411 B2 | 3/2009 | Boesen |
| D601,134 S | 9/2009 | Elabidi et al. |
| 7,825,626 B2 | 11/2010 | Kozisek |
| 7,965,855 B1 | 6/2011 | Ham |
| 7,979,035 B2 | 7/2011 | Griffin et al. |
| 7,983,628 B2 | 7/2011 | Boesen |
| D647,491 S | 10/2011 | Chen et al. |
| 8,095,188 B2 | 1/2012 | Shi |
| 8,108,143 B1 | 1/2012 | Tester |
| 8,140,357 B1 | 3/2012 | Boesen |
| 8,160,265 B2 * | 4/2012 | Mao .................. H04S 7/304 381/309 |
| D666,581 S | 9/2012 | Perez |
| 8,300,864 B2 | 10/2012 | Mullenborn et al. |
| 8,406,448 B2 | 3/2013 | Lin |
| 8,436,780 B2 | 5/2013 | Schantz et al. |
| D687,021 S | 7/2013 | Yuen |
| 8,719,877 B2 | 5/2014 | VonDoenhoff et al. |
| 8,774,434 B2 | 7/2014 | Zhao et al. |
| 8,831,266 B1 | 9/2014 | Huang |
| 8,891,800 B1 | 11/2014 | Shaffer |
| 8,994,498 B2 | 3/2015 | Agrafioti et al. |
| D728,107 S | 4/2015 | Martin et al. |
| 9,013,145 B2 | 4/2015 | Castillo et al. |
| 9,037,125 B1 | 5/2015 | Kadous |
| D733,103 S | 6/2015 | Jeong et al. |
| 9,081,944 B2 | 7/2015 | Camacho et al. |
| 9,510,159 B1 | 11/2016 | Cuddihy et al. |
| D773,439 S | 12/2016 | Walker |
| D775,158 S | 12/2016 | Dong et al. |
| D777,710 S | 1/2017 | Palmborg et al. |
| 9,544,689 B2 | 1/2017 | Fisher et al. |
| D788,079 S | 5/2017 | Son et al. |
| 2001/0005197 A1 | 6/2001 | Mishra et al. |
| 2001/0027121 A1 | 10/2001 | Boesen |
| 2001/0043707 A1 | 11/2001 | Leedom |
| 2001/0056350 A1 | 12/2001 | Calderone et al. |
| 2002/0002413 A1 | 1/2002 | Tokue |
| 2002/0007510 A1 | 1/2002 | Mann |
| 2002/0010590 A1 | 1/2002 | Lee |
| 2002/0030637 A1 | 3/2002 | Mann |
| 2002/0046035 A1 | 4/2002 | Kitahara et al. |
| 2002/0057810 A1 | 5/2002 | Boesen |
| 2002/0076073 A1 | 6/2002 | Taenzer et al. |
| 2002/0118852 A1 | 8/2002 | Boesen |
| 2003/0002705 A1 | 1/2003 | Boesen |
| 2003/0065504 A1 | 4/2003 | Kraemer et al. |
| 2003/0100331 A1 | 5/2003 | Dress et al. |
| 2003/0104806 A1 | 6/2003 | Ruef et al. |
| 2003/0115068 A1 | 6/2003 | Boesen |
| 2003/0125096 A1 | 7/2003 | Boesen |
| 2003/0218064 A1 | 11/2003 | Conner et al. |
| 2004/0070564 A1 | 4/2004 | Dawson et al. |
| 2004/0160511 A1 | 8/2004 | Boesen |
| 2005/0017842 A1 | 1/2005 | Dematteo |
| 2005/0043056 A1 | 2/2005 | Boesen |
| 2005/0094839 A1 | 5/2005 | Gwee |
| 2005/0125320 A1 | 6/2005 | Boesen |

(56) References Cited

U.S. PATENT DOCUMENTS

| | | |
|---|---|---|
| 2005/0148883 A1 | 7/2005 | Boesen |
| 2005/0165663 A1 | 7/2005 | Razumov |
| 2005/0196009 A1 | 9/2005 | Boesen |
| 2005/0251455 A1 | 11/2005 | Boesen |
| 2005/0266876 A1 | 12/2005 | Boesen |
| 2006/0029246 A1 | 2/2006 | Boesen |
| 2006/0073787 A1 | 4/2006 | Lair et al. |
| 2006/0074671 A1 | 4/2006 | Farmaner et al. |
| 2006/0074808 A1 | 4/2006 | Boesen |
| 2006/0166715 A1 | 7/2006 | Engelen et al. |
| 2006/0166716 A1 | 7/2006 | Seshadri et al. |
| 2006/0220915 A1 | 10/2006 | Bauer |
| 2006/0258412 A1 | 11/2006 | Liu |
| 2008/0076972 A1 | 3/2008 | Dorogusker et al. |
| 2008/0090622 A1 | 4/2008 | Kim et al. |
| 2008/0146890 A1 | 6/2008 | LeBoeuf et al. |
| 2008/0187163 A1 | 8/2008 | Goldstein et al. |
| 2008/0253583 A1 | 10/2008 | Goldstein et al. |
| 2008/0254780 A1 | 10/2008 | Kuhl et al. |
| 2008/0255430 A1 | 10/2008 | Alexandersson et al. |
| 2009/0003620 A1 | 1/2009 | McKillop et al. |
| 2009/0008275 A1 | 1/2009 | Ferrari et al. |
| 2009/0017881 A1 | 1/2009 | Madrigal |
| 2009/0073070 A1 | 3/2009 | Rofougaran |
| 2009/0097689 A1 | 4/2009 | Prest et al. |
| 2009/0105548 A1 | 4/2009 | Bart |
| 2009/0154739 A1 | 6/2009 | Zellner |
| 2009/0191920 A1 | 7/2009 | Regen et al. |
| 2009/0245559 A1 | 10/2009 | Boltyenkov et al. |
| 2009/0261114 A1 | 10/2009 | McGuire et al. |
| 2009/0296968 A1 | 12/2009 | Wu et al. |
| 2010/0033313 A1 | 2/2010 | Keady et al. |
| 2010/0203831 A1 | 8/2010 | Muth |
| 2010/0210212 A1 | 8/2010 | Sato |
| 2010/0320961 A1 | 12/2010 | Castillo et al. |
| 2011/0140844 A1 | 6/2011 | McGuire et al. |
| 2011/0239497 A1 | 10/2011 | McGuire et al. |
| 2011/0286615 A1 | 11/2011 | Olodort et al. |
| 2012/0057740 A1 | 3/2012 | Rosal |
| 2013/0316642 A1 | 11/2013 | Newham |
| 2013/0346168 A1 | 12/2013 | Zhou et al. |
| 2014/0079257 A1 | 3/2014 | Ruwe et al. |
| 2014/0106677 A1 | 4/2014 | Altman |
| 2014/0122116 A1 | 5/2014 | Smythe |
| 2014/0153768 A1 | 6/2014 | Hagen et al. |
| 2014/0163771 A1 | 6/2014 | Demeniuk |
| 2014/0185828 A1 | 7/2014 | Helbling |
| 2014/0219467 A1 | 8/2014 | Kurtz |
| 2014/0222462 A1 | 8/2014 | Shakil et al. |
| 2014/0235169 A1 | 8/2014 | Parkinson et al. |
| 2014/0270227 A1 | 9/2014 | Swanson |
| 2014/0270271 A1 | 9/2014 | Dehe et al. |
| 2014/0335908 A1 | 11/2014 | Krisch et al. |
| 2014/0348367 A1 | 11/2014 | Vavrus et al. |
| 2015/0028996 A1 | 1/2015 | Agrafioti et al. |
| 2015/0035643 A1 | 2/2015 | Kursun |
| 2015/0036835 A1 | 2/2015 | Chen |
| 2015/0110587 A1 | 4/2015 | Hori |
| 2015/0148989 A1 | 5/2015 | Cooper et al. |
| 2015/0245127 A1 | 8/2015 | Shaffer |
| 2015/0366471 A1* | 12/2015 | LeBoeuf ............... A61B 5/0059 600/301 |
| 2015/0373467 A1 | 12/2015 | Gelter |
| 2015/0373474 A1 | 12/2015 | Kraft et al. |
| 2016/0033280 A1 | 2/2016 | Moore et al. |
| 2016/0072558 A1 | 3/2016 | Hirsch et al. |
| 2016/0073189 A1 | 3/2016 | Lindén et al. |
| 2016/0125892 A1 | 5/2016 | Bowen et al. |
| 2016/0256082 A1* | 9/2016 | Ely ....................... A61B 5/0024 |
| 2016/0353196 A1 | 12/2016 | Baker et al. |
| 2016/0360350 A1 | 12/2016 | Watson et al. |
| 2017/0059152 A1 | 3/2017 | Hirsch et al. |
| 2017/0060262 A1 | 3/2017 | Hviid et al. |
| 2017/0060269 A1 | 3/2017 | Förstner et al. |
| 2017/0061751 A1 | 3/2017 | Loermann et al. |
| 2017/0062913 A1 | 3/2017 | Hirsch et al. |
| 2017/0064426 A1 | 3/2017 | Hviid |
| 2017/0064428 A1 | 3/2017 | Hirsch |
| 2017/0064432 A1 | 3/2017 | Hviid et al. |
| 2017/0064437 A1 | 3/2017 | Hviid et al. |
| 2017/0078780 A1 | 3/2017 | Qian et al. |
| 2017/0078785 A1 | 3/2017 | Qian et al. |
| 2017/0108918 A1 | 4/2017 | Boesen |
| 2017/0109131 A1 | 4/2017 | Boesen |
| 2017/0110124 A1 | 4/2017 | Boesen et al. |
| 2017/0110899 A1 | 4/2017 | Boesen |
| 2017/0111723 A1 | 4/2017 | Boesen |
| 2017/0111725 A1 | 4/2017 | Boesen et al. |
| 2017/0111726 A1 | 4/2017 | Martin et al. |
| 2017/0111740 A1 | 4/2017 | Hviid et al. |
| 2017/0127168 A1 | 5/2017 | Briggs et al. |
| 2017/0142511 A1 | 5/2017 | Dennis |
| 2017/0151447 A1 | 6/2017 | Boesen |
| 2017/0151668 A1 | 6/2017 | Boesen |
| 2017/0151918 A1 | 6/2017 | Boesen |
| 2017/0151930 A1 | 6/2017 | Boesen |
| 2017/0151957 A1 | 6/2017 | Boesen |
| 2017/0151959 A1 | 6/2017 | Boesen |
| 2017/0153114 A1 | 6/2017 | Boesen |
| 2017/0153636 A1 | 6/2017 | Boesen |
| 2017/0154532 A1 | 6/2017 | Boesen |
| 2017/0155985 A1 | 6/2017 | Boesen |
| 2017/0155992 A1 | 6/2017 | Perianu et al. |
| 2017/0155993 A1 | 6/2017 | Boesen |
| 2017/0155997 A1 | 6/2017 | Boesen |
| 2017/0155998 A1 | 6/2017 | Boesen |
| 2017/0156000 A1 | 6/2017 | Boesen |
| 2017/0178631 A1 | 6/2017 | Boesen |
| 2017/0180842 A1 | 6/2017 | Boesen |
| 2017/0180843 A1 | 6/2017 | Perianu et al. |
| 2017/0180897 A1 | 6/2017 | Perianu |
| 2017/0188127 A1 | 6/2017 | Perianu et al. |
| 2017/0188132 A1 | 6/2017 | Hirsch et al. |
| 2017/0193978 A1 | 7/2017 | Goldman |
| 2017/0195829 A1 | 7/2017 | Belverato et al. |
| 2017/0208393 A1 | 7/2017 | Boesen |
| 2017/0214987 A1 | 7/2017 | Boesen |
| 2017/0215016 A1 | 7/2017 | Dohmen et al. |
| 2017/0230752 A1 | 8/2017 | Dohmen et al. |
| 2017/0239551 A1* | 8/2017 | Pease ................... A43B 3/0005 |
| 2017/0251933 A1 | 9/2017 | Braun et al. |
| 2017/0257698 A1 | 9/2017 | Boesen et al. |
| 2017/0263236 A1 | 9/2017 | Boesen et al. |
| 2017/0273622 A1 | 9/2017 | Boesen |
| 2018/0085068 A1* | 3/2018 | Telfort .................. A61B 7/04 |

FOREIGN PATENT DOCUMENTS

| | | |
|---|---|---|
| CN | 104837094 A | 8/2015 |
| EP | 1469659 A1 | 10/2004 |
| EP | 1017252 A3 | 5/2006 |
| EP | 2903186 A1 | 8/2015 |
| GB | 2074817 | 4/1981 |
| GB | 2508226 A | 5/2014 |
| WO | 2008103925 A1 | 8/2008 |
| WO | 2007034371 A3 | 11/2008 |
| WO | 2011001433 A2 | 1/2011 |
| WO | 2012071127 A1 | 5/2012 |
| WO | 2013134956 A1 | 9/2013 |
| WO | 2014046602 A1 | 3/2014 |
| WO | 2014043179 A3 | 7/2014 |
| WO | 2015061633 A2 | 4/2015 |
| WO | 2015110577 A1 | 7/2015 |
| WO | 2015110587 A1 | 7/2015 |
| WO | 2016032990 A1 | 3/2016 |

OTHER PUBLICATIONS

Akkermans, "Acoustic Ear Recognition for Person Identification", Automatic Identification Advanced Technologies, 2005 pp. 219-223.

Announcing the $3,333,333 Stretch Goal (Feb. 24, 2014).

(56) References Cited

OTHER PUBLICATIONS

Ben Coxworth: "Graphene-based ink could enable low-cost, foldable electronics", "Journal of Physical Chemistry Letters", Northwestern University, (May 22, 2013).
Blain: "World's first graphene speaker already superior to Sennheiser MX400", htt://www.gizmag.com/graphene-speaker-beats-sennheiser-mx400/31660, (Apr. 15, 2014).
BMW, "BMW introduces BMW Connected—The personalized digital assistant", "http://bmwblog.com/2016/01/05/bmw-introduces-bmw-connected-the-personalized-digital-assistant", (Jan. 5, 2016).
BRAGI is on Facebook (2014).
BRAGI Update—Arrival of Prototype Chassis Parts—More People—Awesomeness (May 13, 2014).
BRAGI Update—Chinese New Year, Design Verification, Charging Case, More People, Timeline(Mar. 6, 2015).
BRAGI Update—First Sleeves From Prototype Tool—Software Development Kit (Jun. 5, 2014).
BRAGI Update—Let's Get Ready to Rumble, A Lot to be Done Over Christmas (Dec. 22, 2014).
BRAGI Update—Memories From April—Update on Progress (Sep. 16, 2014).
BRAGI Update—Memories from May—Update on Progress—Sweet (Oct. 13, 2014).
BRAGI Update—Memories From One Month Before Kickstarter—Update on Progress (Jul. 10, 2014).
BRAGI Update—Memories From the First Month of Kickstarter—Update on Progress (Aug. 1, 2014).
BRAGI Update—Memories From the Second Month of Kickstarter—Update on Progress (Aug. 22, 2014).
BRAGI Update—New People @BRAGI—Prototypes (Jun. 26, 2014).
BRAGI Update—Office Tour, Tour to China, Tour to CES (Dec. 11, 2014).
BRAGI Update—Status on Wireless, Bits and Pieces, Testing-Oh Yeah, Timeline(Apr. 24, 2015).
BRAGI Update—The App Preview, The Charger, The SDK, BRAGI Funding and Chinese New Year (Feb. 11, 2015).
BRAGI Update—What We Did Over Christmas, Las Vegas & CES (Jan. 19, 2014).
BRAGI Update—Years of Development, Moments of Utter Joy and Finishing What We Started(Jun. 5, 2015).
BRAGI Update—Alpha 5 and Back to China, Backer Day, on Track(May 16, 2015).
BRAGI Update—Beta2 Production and Factory Line(Aug. 20, 2015).
BRAGI Update—Certifications, Production, Ramping Up, (Nov. 13, 2015).
BRAGI Update—Developer Units Shipping and Status(Oct. 5, 2015).
BRAGI Update—Developer Units Started Shipping and Status (Oct. 19, 2015).
BRAGI Update—Developer Units, Investment, Story and Status(Nov. 2, 2015).
BRAGI Update—Getting Close(Aug. 6, 2015).
BRAGI Update—On Track, Design Verification, How it Works and What's Next(Jul. 15, 2015).
BRAGI Update—On Track, on Track and Gems Overview, (Jun. 24, 2015).
BRAGI Update—Status on Wireless, Supply, Timeline and Open House@BRAGI(Apr. 1, 2015).
BRAGI Update—Unpacking Video, Reviews on Audio Perform and Boy are We Getting Close(Sep. 10, 2015).
Healthcare Risk Management Review, "Nuance updates computer-assisted physician documentation solution" (Oct. 20, 2016).
Hoffman, "How to Use Android Beam to Wirelessly Transfer Content Between Devices", (Feb. 22, 2013).
Hoyt et. al., "Lessons Learned from Implementation of Voice Recognition for Documentation in the Military Electronic Health Record System", The American Health Information Management Association (2017).
Hyundai Motor America, "Hyundai Motor Company Introduces a Health + Mobility Concept for Wellness in Mobility", Fountain Valley, Californa (2017).
International Search Report & Written Opinion, PCT/EP2016/070231 (dated Nov. 18, 2016).
Last Push Before the Kickstarter Campaign Ends on Monday 4pm CET (Mar. 28, 2014).
Nigel Whitfield: "Fake tape detectors, 'from the stands' footie and UGH? Internet of Things in my set-top box"; http://www.theregister.co.uk/2014/09/24/ibc_round_up_object_audio_dlna_iot/ (Sep. 24, 2014).
Nuance, "ING Netherlands Launches Voice Biometrics Payment System in the Mobile Banking App Powered by Nuance", "https://www.nuance.com/about-us/newsroom/press-releases/ing-netherlands-launches-nuance-voice-biometrics.html", 4 pages (Jul. 28, 2015).
Staab, Wayne J., et al., "A One-Size Disposable Hearing Aid is Introduced", The Hearing Journal 53(4):36-41) Apr. 2000.
Stretchgoal—It's Your Dash (Feb. 14, 2014).
Stretchgoal—The Carrying Case for the Dash (Feb. 12, 2014).
Stretchgoal—Windows Phone Support (Feb. 17, 2014).
The Dash + The Charging Case & The BRAGI News (Feb. 21, 2014).
The Dash—A Word From Our Software, Mechanical and Acoustics Team + An Update (Mar. 11, 2014).
Update From BRAGI—$3,000,000—Yipee (Mar. 22, 2014).
Wertzner et al., "Analysis of fundamental frequency, jitter, shimmer and vocal intensity in children with phonological disorders", V. 71, n.5, 582-588, Sep./Oct. 2005; Brazilian Journal of Othrhinolaryngology.
Wikipedia, "Gamebook", https://en.wikipedia.org/wiki/Gamebook, Sep. 3, 2017, 5 pages.
Wikipedia, "Kinect", "https://en.wikipedia.org/wiki/Kinect", 18 pages, (Sep. 9, 2017).

* cited by examiner

3D SOUND POSITIONING WITH DISTRIBUTED SENSORS

PRIORITY STATEMENT

This application claims priority to U.S. Provisional Patent Application 62/416,587, filed on Nov. 2, 2016, and entitled 3D Sound positioning with distributed sensors, hereby incorporated by reference in its entirety.

FIELD OF THE INVENTION

The present invention relates to wearable devices. More particularly, but not exclusively, the present invention relates to earpieces.

BACKGROUND

What is needed are methods and systems for wearable devices. In particular methods and systems which allow for increased functionality for earpieces when used in combination with other wearable devices.

SUMMARY

Therefore, it is a primary object, feature, or advantage of the present invention to improve over the state of the art.

It is a further object, feature, or advantage of the present invention to provide audiometric feedback in a three-dimensional manner from body sensor signals.

It is a still further object, feature, or advantage of the present invention to locate a body sensor using a multitude of different methods.

According to one aspect, a method of providing audiometric feedback from a network of distributed body sensors using one or more earpieces is provided. The method includes receiving signals from the network of distributed body sensors at the one or more wireless earpieces, processing the signals received at the one or more wireless earpieces to determine a location of individual body sensors within the network of distributed body sensors relative the one or more earpieces, and producing audiometric feedback at the one or more wireless earpieces at least partially based on the locations of the individual body sensors relative to the one or more earpieces. The signals may be sound signals. The audiometric feedback may be based on changes in the location of the individual body sensors relative to the one or more earpieces due to movement. The audio metric feedback may include an audiometric rhythmic signal synchronized to the movement. The method may further include encoding sensor information from the individual body sensors within the sound signals and decoding the sensor information from the individual body sensors at the one or more wireless earpieces. Alternatively, the signals may be communicated over skin of a user of the distributed body sensors and the one or more earpieces. One or more of the distributed body sensors may be associated with an article of clothing. One or more of the distributed body sensors may be associated with a band.

In one implementation, a system includes an earpiece having an earpiece housing, a processor disposed within the earpiece housing, a microphone operatively connected to the earpiece housing and the processor, wherein the microphone is configured to receive voice commands, a wireless transceiver operatively connected to the earpiece housing and the processor, wherein the wireless transceiver is configured to receive a signal from at least one body sensor, and a speaker operatively connected to the earpiece housing and the processor, wherein the speaker is configured to provide audiometric feedback from one or more body sensors in a three-dimensional manner.

One or more of the follow features may be included. The earpiece may comprise a set of earpieces. The set of earpieces may comprise a left earpiece and a right earpiece. The earpiece housing may be composed of soundproof materials. The earpiece housing may be configured to substantially enclose an ear canal. The earpiece housing may be further configured to substantially fit within the ear canal. The earpiece housing may also have a sheath attached to a side proximate to the ear canal. The wireless transceiver of the left earpiece and the wireless transceiver of the right earpiece may be configured to triangulate a position of one or more body sensors from the signal. A gestural control interface may be operatively connected to the earpiece housing and the processor. The gestural control interface may be further configured to reconfigure the processor, the microphone, or the wireless transceiver in response to a gesture. A sensor may be operatively connected to the earpiece housing and the processor, wherein the sensor may be configured to determine the position of one or more body sensors operatively connected to the user. The sensor may be configured to sense one or more motions of the user. A bone conduction microphone may be positioned along a temporal bone and may be configured to receive body sounds from the user. The processor may be configured to provide noise cancellation sound at the speaker, wherein the noise cancellation sound may be configured to substantially neutralize one or more body sounds via destructive interference. The speaker may be configured to short out if the decibel level of the audiometric feedback exceeds a certain level.

In another implementation, a method of determining a position of a body sensor using a set of earpieces having a left earpiece and a right earpiece includes receiving an audio signal from the body sensor at a microphone disposed within the left earpiece and a microphone disposed within the right earpiece, wherein the signal at the left earpiece has a first arrival time and a first angle of incidence and the signal at the right earpiece has a second arrival time and a second angle of incidence, transmitting the first arrival time and the first angle of incidence to the wireless transceiver of the right earpiece via the wireless transceiver of the left earpiece, and triangulating the position of the body sensor from the first arrival time, second arrival time, first angle of incidence and the second angle of incidence using a processor operatively connected to the right earpiece.

One or more of the following features may be included. At least one signal may encode data related to the user. The data may be position or motion data. Audiometric feedback may be created from the position or motion data. Audiometric feedback may also be provided using a speaker operatively connected to the right earpiece, and the audiometric feedback may be provided in a three-dimensional manner.

In another implementation, a method of determining a position of a body sensor using a plurality of microphones operatively connected to an earpiece includes transmitting a sound signal using a speaker operatively connected to the earpiece, receiving a reflected sound signal at the plurality of microphones, and determining the position of the body sensor from a sound intensity differential between the reception of the reflected sound at a first microphone and the reception of the reflected sound at a second microphone and a time delay between the reception of the reflected sound at the first microphone and the reception of the reflected sound at the second microphone.

One or more of the following features may be included. The sound signal may be transmitted through the user. The sound signal may be modulated. The reflected sound signal may be correlated with the sound signal using pulse compression.

In another implementation, a method of providing audiometric feedback from a body sensor using an earpiece includes receiving a signal from the body sensor, processing information encoded in the signal using a processor disposed within the earpiece, and producing audiometric feedback derived from the information encoded in the signal in a three-dimensional manner.

One or more of the following features may be included. Body sounds may be received via a bone conduction microphone operatively connected to the earpiece. Noise cancellation sound may be provided using a processor operatively connected to the earpiece, wherein the noise cancellation sound is configured to substantially neutralize the body sounds via destructive interference. The information encoded in the signal may comprise kinematic information. The audiometric feedback may be synchronized to the kinematic information. Audiometric feedback derived from the kinematic information may lead the user.

One or more of these and/or other objects, features, or advantages of the present invention will become apparent from the specification and claims that follow. No single embodiment need provide each and every object, feature, or advantage. Different embodiments may have different objects, features, or advantages. Therefore, the present invention is not to be limited to or by an object, feature, or advantage stated herein.

DETAILED DESCRIPTION

A network of distributed sensors which may be wearable devices (such as shoes, clothing, and socks) is provided. Sensors may be placed on the various wearable devices at various different positions within the body. The position of the sensors on the body is determined. Audiometric feedback may be provided. One example is to produce an audiometric rhythmic signal which can synchronize to a person's movement or lead a person's movements.

Figure 1:
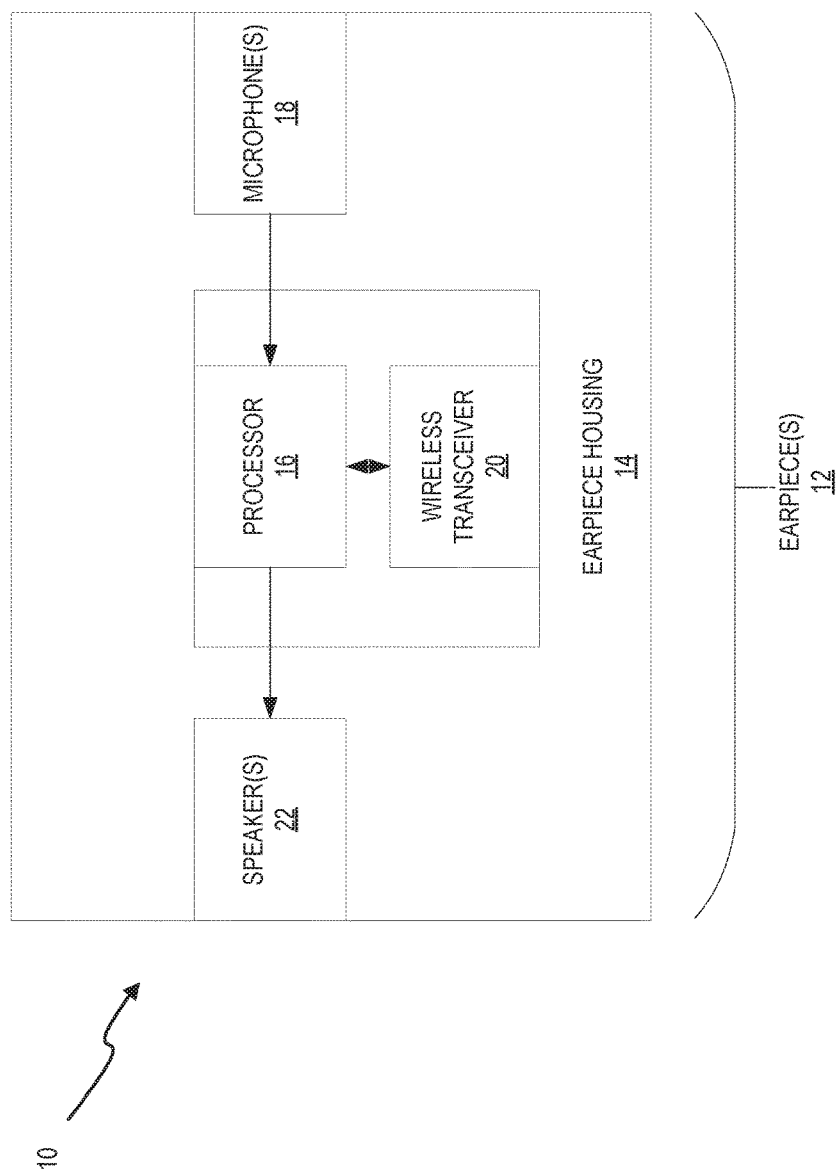
FIG. 1 illustrates a block diagram of one embodiment of the system.

FIG. 1 illustrates one embodiment of a system 10 which includes an earpiece 12 having an earpiece housing 14, a processor 16 disposed within the earpiece housing 14, a microphone 18 operatively connected to the processor 16, a wireless transceiver 20 disposed within the earpiece housing 14 and operatively connected to the processor 16, and a speaker 22 disposed within the earpiece housing 14 and operatively connected to the processor 16. The earpiece housing 14 may be composed of soundproof materials or any material that is resistant to shear and strain and may also have a sheath attached in order to improve comfort, sound transmission, or reduce the likelihood of skin or ear allergies. In addition, the earpiece housing 14 may also substantially encompass the outer opening of the ear canal of a user in order to substantially reduce or eliminate external sounds.

The processor 16 may be configured to process the signals received from the body sensor, wherein the signals may encode for sound, instructions, or information which may be stored within a data storage device, transmitted to another electronic device, or provided to the user or a third party via the speaker 22. The processor 16 may also process inputs received from the microphone 18 or another external electronic device and store the inputs in a data storage device or communicate them to the user or a third party via the speaker 22.

The microphone 18, may be positioned to receive certain ambient sounds. For example, where body worn devices within a network of body worn sensors communicate with the earpiece by emitting sounds, the microphone 18 may be used to detect these sounds. Such sounds may be emitted at a frequency higher than human hearing such as over 20 kHz and the microphone may be configured to detect sounds of such frequencies.

The wireless transceiver 20 may be configured to receive one or more signals from a wearable device or another electronic device. In one embodiment the wireless transceiver 20 may provide for wireless radio signals such as Bluetooth, BLE, or other types of radio signals. The signals from each source may be received in any order and may be received simultaneously. For example, the wireless transceiver 20 may receive one signal from a body sensor related to kinetic information in regards to one of the user's feet, receive another signal from an external electronic device which may encode information related to a topic of interest of the user, and receive yet another signal from someone trying to call the user. The signals received by the wireless transceiver 20 may travel through the air, may be sent as sound signals, or may communicated through the user's skin.

The speaker 22, in addition to being operatively connected to the processor 16, may be used to provide audiometric feedback in a three-dimensional manner by reproducing audio generated by the wireless earpiece. For example, the audio may provide motion feedback either from one or more body sensors and/or provide feedback created by the processor 16 from data received from one or more body sensors that the user's feet are not properly aligned or that the user's gait is not optimal. The audiometric feedback may be provided in such a manner that the user interprets the feet-related feedback as emanating from the ground, or the gait feedback as emanating from the user's upper legs. This may be performed by generating three-dimensional sound and setting sound source locations appropriately to provide the desired effect on the user's perception of the sound. The speaker 22 may also be used to produce music, sounds, instructions, or information originating from a signal of a wearable device, a signal from another electronic device, the microphone 18 or a data storage device. For example, the speaker 22 may produce a song, a sound, a podcast, a newscast, a forecast, or anything else of interest to the user selected from a menu by the user or third party, which may be prompted by a voice command or a gesture. The speaker 22 may also communicate a notification of the choice the user or a third party selected so that the user or third party may change the selection if an error was made.

Figure 2:
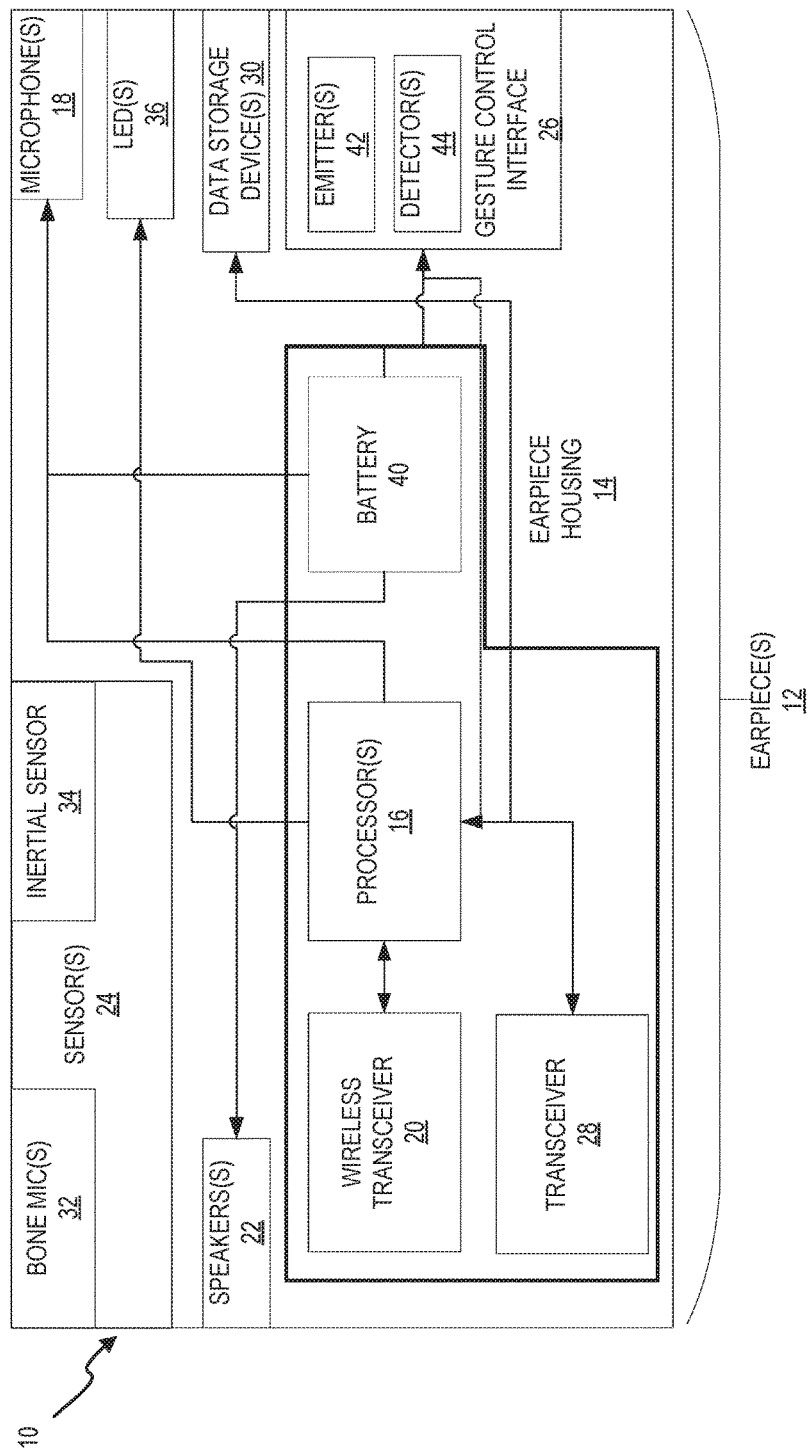
FIG. 2 illustrates a block diagram of a second embodiment of the system.

FIG. 2 illustrates another embodiment of the system 10 comprising an earpiece 12 having an earpiece housing 14, a processor 16 disposed within the earpiece housing 14, at least one microphone 18 operatively connected to the processor 16, a wireless transceiver 20 operatively connected to the processor 16, a speaker 22 operatively connected to the processor 16, a sensor 24 which may comprise an bone conduction microphone 32 and/or an inertial sensor 34, a gesture control interface 26 with at least one emitter 42 and at least one detector 44 operatively connected to the processor 16, a transceiver 28 disposed within the earpiece housing 14, a data storage device 30 operatively connected to the processor 16, and at least one LED 36, and a battery 40 disposed within the earpiece housing 14 and operatively connected to various components.

The earpiece housing 14 may be composed of one or more metal or plastic materials that are substantially resistant to straining and shearing stresses and may also have a sheath attached in order to improve comfort, sound transmission, or reduce the likelihood of skin or ear allergies. In addition, the earpiece housing 14 may also substantially encompass an outer opening of a user's ear canal in order to substantially reduce or eliminate external sounds to further improve audio transparency and may be also be configured to substantially fit with the user's ear canal to facilitate audio transmission. The earpiece housing may be an ear bud style configuration.

A processor 16 may be disposed within the earpiece housing 14 and may be configured to process one or more signals from one or more body sensors, one or more signals from another wearable device, process voice commands from a user or a third party, process one or more signals from the wireless transceiver 20, process one or more signals from the transceiver 28, process one or more signals originating from the data storage device 30, process one or more signals from the bone conduction microphone 32, or process one or more signals from the inertial sensor 34, wherein the signals may encode for music, newscasts, podcasts, commentary, instructions, information related to sensor readings, or other forms of digital media and/or information. The processor 16 may also, in addition to processing the aforementioned signals, produce the signals from the microphone 18, the wireless transceiver 20, the transceiver 28, the data storage device 30, the bone conduction microphone 32, or the inertial sensor 34 at the speaker 22. The processor 16 may also be reconfigured by the user or a third party through the use of gestures read by a gestural control interface 26, a voice command received by one or more microphones 18, or a signal received by the wireless transceiver 20 or the transceiver 28.

One or more microphones 18 may be operatively connected to the earpiece housing 14 and the processor 16 and may be configured to receive one or more voice commands which may be used to cease, commence, change, or modify one or more functions of the earpiece 12. For example, a voice command to cease receiving ambient sounds may be provided by the user or a third party saying, "Cease reception of outside sounds," or a voice command to play the fifth song in a playlist may be provided by the user or a third party saying, "Play song five in playlist," or "Skip to song five." Other commands may be used to cease, commence, change or modify other functions of the earpiece 12. In addition, one or more microphones 18 may also be configured to receive ambient sounds from one or more outside sources, which may originate from the user, a third party, a machine, an animal, another earpiece, another electronic device, or even nature itself. The ambient sounds received by the microphone 18 may include a word, a combination of words, a sound, a combination of sounds, or any combination of the aforementioned. The sounds may be of any frequency and need not necessarily be audible to the user and may be used to reconfigure one or more components of the earpiece 12.

A wireless transceiver 20 may be disposed within the earpiece housing 14 and operatively connected to the processor 16 and may be configured to, in addition to receiving one or more signals from a body sensor, receive one or more signals from and transmit one or more signals to at least one wearable device, and/or receive one or more signals from one or more external electronic devices. All of the aforementioned signals may be transmitted to the processor 16 for further processing. The external electronic devices the wireless transceiver 20 may be configured to receive signals from include Bluetooth devices, mobile devices, desktops, laptops, tablets, modems, routers, communications towers, cameras, watches, third-party earpieces, earpieces, or other electronic devices capable of transmitting or receiving wireless signals. The signals received by the wireless transceiver 20 may encode for sound, instructions, or information. The wireless transceiver 20 may receive or transmit more than one signal simultaneously.

A speaker 22 may be operatively connected to the processor 16 and, in addition to being configured to provide audiometric feedback in a three-dimensional manner, may be configured to produce one or more ambient and/or non-ambient sounds from one or more microphones 16 or produce audio output derived from one or more signals from the wireless transceiver 20, the transceiver 28, or the data storage device 30. The produced sounds may consist of musical sounds, non-musical sounds, commentary, instructions, miscellaneous information, or anything else of interest or importance to the user.

One or more sensors 24 may be operatively connected to the earpiece housing 14 and the processor 16 and may be configured to sense at least one user motion and may also be configured to read sounds or motions that may not be ascertainable by other components of the earpiece 12. For example, a bone conduction microphone 32 may be configured to receive body sounds from the temporal bone of the user's skull and transmit the body sounds to the processor 16, which may then create a noise cancellation sound configured to substantially neutralize each unique body sound the processor 16 receives using destructive interference techniques. An inertial sensor 34 may also be employed to ascertain the movement of the user. For example, the inertial sensor 34 may sense a running speed of the user or an arm speed of a third party which may be communicated to the processor 16, which may be used in providing audiometric feedback related to an athletic or personal goal of the user. Each sensor 24 may be positioned at any location on the earpiece housing 14 conducive to receiving information and need not necessarily be in direct contact with either the user or the external environment.

A gesture control interface 26 having at least one emitter 42 and a detector 44 may be operatively connected to the earpiece housing 14 and the processor 16 and may be configured to allow the user or a third party to control one or more functions of the earpiece 12. For example, a menu may be prompted through the use of a gesture with the gestural control interface 26, which may allow the user or a third party to listen to a song either stored within the data storage device 30 or received through the wireless transceiver 20, listen to a playlist, newscast, podcast, or a weather report received through the wireless transceiver 20 or stored within the data storage device 30, obtain information on the user's current surroundings, or anything else that may be of interest to the user or a third party, and the aforementioned list is non-exclusive. The selections may be chosen through the use of one or more additional gestures or through the use of one or more voice commands from the user and/or a third party. The types of gestures that may be used with the gesture control interface 26 to control the earpiece 12 include, without limitation, touching, tapping, swiping, use of an instrument, or any combination of the aforementioned gestures. Touching gestures used to control the earpiece 12 may be of any duration and may include the touching of areas that are not part of the gesture control interface 26. Tapping gestures used to control the earpiece 12 may include one or more taps and need not be brief. Swiping gestures used to control the earpiece 12 may include a single swipe, a swipe that changes direction at least once, a swipe with a time delay, a plurality of swipes, or any combination of the aforementioned.

A transceiver 28 may be disposed within the earpiece housing 14 and may be configured to receive signals from and to transmit signals to a second earpiece of the user if the user is using more than one earpiece. The transceiver 28 may receive or transmit more than one signal simultaneously. The transceiver 28 may be of any number of types including a near field magnetic induction (NFMI) transceiver.

One or more data storage devices 30 may be operatively connected to the earpiece housing 14 and the processor 16 and may be configured to store data or information related to one or more signals received from a wearable device, body sensor, external electronic device, or a combination of the aforementioned. One or more data storage devices 30 may also have one or more programs preinstalled which may be (1) used by the processor 16 in processing one or more signals, (2) used by the processor 16 in executing one or more commands to be carried out by one or more components of the earpiece 12, (3) accessible via a gesture or voice command, or (4) transmitted to an external electronic device.

One or more LEDs 36 may be operatively connected to the processor 16 and may be configured to emit light in order to convey information to a user concerning the earpiece 12. The LEDs 36 may be located in any area on the earpiece 12 suitable for viewing by the user or a third party and may consist of as few as one diode which may be provided in combination with a light guide. In addition, the LEDs 36 may be discernable by a human eye or an electronic device and need not have a minimum luminescence.

Figure 3:
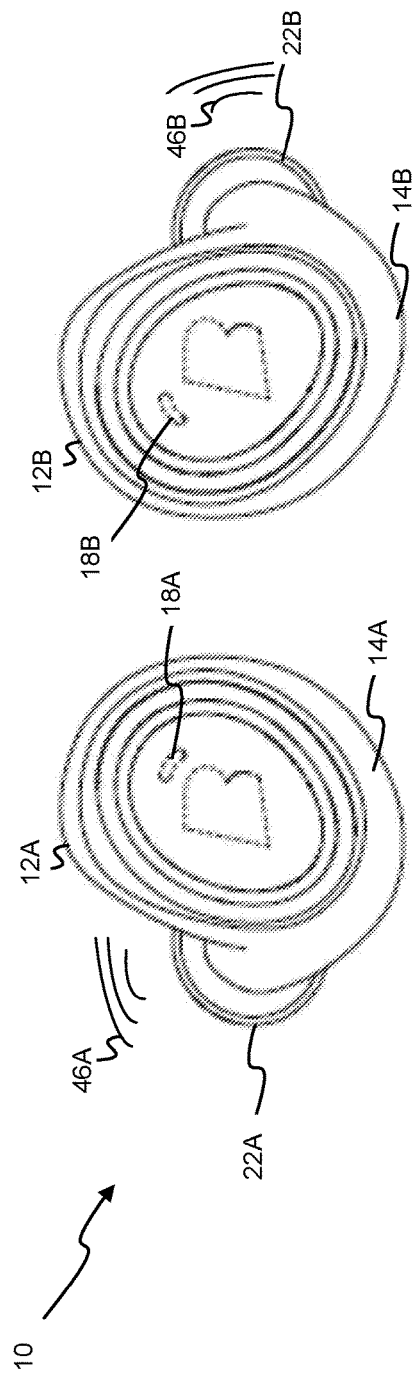
FIG. 3 illustrates a left earpiece and a right earpiece.

FIG. 3 illustrates a pair of earpieces 12 which includes a left earpiece 12A and a right earpiece 12B. The left earpiece 12A has a left earpiece housing 14A. The right earpiece 12B has a right earpiece housing 14B. The left earpiece 12A and the right earpiece 12B may be configured to substantially encompass an outer opening of a user's ear canal in order to substantially prevent external sounds from reaching the user's ear canal and/or fit within the user's ear canal in order to minimize the distance between the speakers and a user's tympanic membranes. The earpiece housings 14A and 14B may be composed of metallic materials, plastic materials, or any material with substantial shear and strain resistance and may also be configured to be soundproof in order to improve audio transparency. A microphone 18A is shown on the left earpiece 12A and a microphone 18B is shown on the right earpiece 12B. The microphones 18A and 18B may be located anywhere on the left earpiece 12A and the right earpiece 12B respectively and each microphone may be configured to receive one or more voice commands. Speakers 22A and 22B may be configured to communicate audiometric feedback 46A and 46B.

Various methods may be used for determining a position of a body sensor using a set of earpieces having a left earpiece and a right earpiece. For example, a signal from the body sensor may be received by both a wireless transceiver disposed within the left earpiece and a wireless transceiver disposed within the right earpiece. The signal may arrive at each wireless transceiver at different times and at different angles of incidence. The body sensors transmitting the signal may either be directly worn by a user or may be part of another wearable device such as a watch or item of clothing. The signal transmitted by the body sensor may encode positional data related to the user (for example, it may indicate that it is worn on a left side of the body or right side of the body), kinetic or motion data related to the user, data or information related to persons, animals, or objects adjacent to the user, terrain data, health data related to the user, weather data, data or information related to a task or goal of the user or a third party, or anything else a body sensor is capable of sensing. In addition, signals from more than one body sensor may be received by the wireless transceivers. For example, a body sensor located on the user's foot may sense and transmit a signal with information concerning the user's speed or gait, another body sensor located on the user's chest may sense the user's heart rate or objects that are related to the user's goal, such as a building along a jogging route that also acts as a checkpoint for the user's progress, and another body sensor located on the user may relay terrain information of the user's immediate vicinity. The signals transmitted by the body sensors may also be transmitted galvanically through the user's skin and may be received by the wireless transceivers at any point in time and may be received in any order. Where communicated through the user's skin, electrical contact areas may be present on both the wearable devices as well as one or more earpieces. In addition, the signals may be transmitted through generating audio transmissions which are outside of the range of a person's normal hearing but may be captured with microphones within the earpieces. In addition, signals from two or more body sensors may reach the wireless transceivers at different times and rates.

In one embodiment the arrival time and the angle of incidence of the signal received by the left earpiece may be transmitted to the right earpiece via wireless transceiver. Alternatively, the arrival time and the angle of incidence of the signal received by the right earpiece may be transmitted to the left earpiece via wireless transceiver, or both earpieces may transmit their signal data to the other earpiece. The transmission of the arrival time or the angle of incidence to the other processor may be performed continuously or discretely, and the information may be transmitted in any order. A processor disposed within one of the earpieces uses the two arrival times and the two angles of incidence to determine the position of a body sensor using triangulation algorithms, direction finding techniques or otherwise. Other algebraic or geometric techniques may also be employed to determine the position of the body sensor. The processor may receive more than one reading from a body sensor or receive multiple readings from multiple body sensors operatively connected to the user; in fact, the position of a body sensor may be a position function when the user is in motion, with time as the independent variable and position as the dependent variable.

Figure 4:
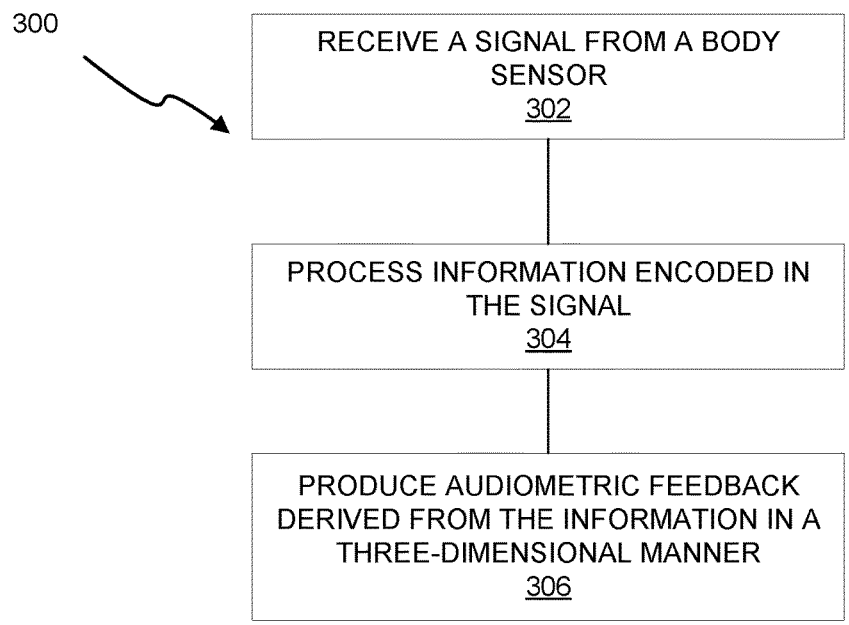
FIG. 4 illustrates a flowchart of a method of providing audiometric feedback from a body sensor using an earpiece.

FIG. 4 illustrates a flowchart of a method of providing audiometric feedback from a body sensor using an earpiece 300. First, in step 302, a signal is received from the body sensor at the earpiece. More than one signal or signals from multiple body sensors may be received, and the signals may be received continuously or intermittently. The signals may encode data related to user position, user motion, user health, tasks, goals, persons, animals, objects, terrain, weather or anything else that a body sensor may be capable of sensing. For example, a signal may encode data related to the user's body temperature and heart rate, or may encode lower body motion data for further analysis.

In step 304, a processor operatively connected to the earpiece processes data or information encoded in the signal received from the body sensor. The processor may be any number of different processors or combinations of processors. More than one signal or one body sensor may be involved, and the processor may process the signals it receives in any particular order. The processor may create audiometric feedback derived from the data or information encoded in the signals it receives, wherein the audiometric feedback may be related to running speed, jogging speed, user gait, body temperature, heart rate, blood sugar, electrolytes, body moisture, current temperature, current obstacles, checkpoints, goals, tasks, or anything else that a body sensor may sense or the user may desire. The processor may also process signals from a data storage device operatively connected to the processor or an external electronic device, wherein the signals may encode for music, sound, instructions, information or other media or informational-related topics, and may incorporate the signals in the audiometric feedback. For example, the processor may integrate instructions to take a rest stop stored in the data storage device with instructions on how to reach the rest stop into the audiometric feedback if both the current temperature and the body temperature exceed a specified value. In addition, the processor may incorporate certain sounds or music cues into the audiometric feedback if certain milestones have been met or certain checkpoints have been reached. The processor may also create noise cancellation sounds for any bodily-related sounds that may distract the user. The bodily-related sounds may originate from any part of the user's body and may also include any clothing or jewelry the user is wearing or any objects the user may be carrying.

In step 306, the processor produces the audiometric feedback derived from the encoded information at a speaker operatively connected to the earpiece. The audiometric feedback may be provided in a three-dimensional manner. For example, if the user is listening to an instructional audio detailing how to properly swing a golf club and the user's feet placement is incorrect or otherwise suboptimal, the user may hear, "spread your feet six more inches" as if the feedback originated from the user's feet. In addition, the audiometric feedback may be produced in such a manner as to synchronize with the user's movements or lead the user. For example, if the user is listening to an instructional dancing audio, three-dimensional audiometric feedback may be provided that synchronizes with the dance movements. In addition, if the user is listening to a workout routine which is configured to operate with one or more body sensors present on the user's body, sound cues may be provided to lead the user as to proper body movement or proper body mechanics in order to optimize the workout. Additional feedback, music, sound, instructions, information, or other media-related output unrelated to a body sensor may also be produced at the speaker, and the speaker may short out if the sound level at any point exceeds a certain sound intensity threshold.

Figure 5:
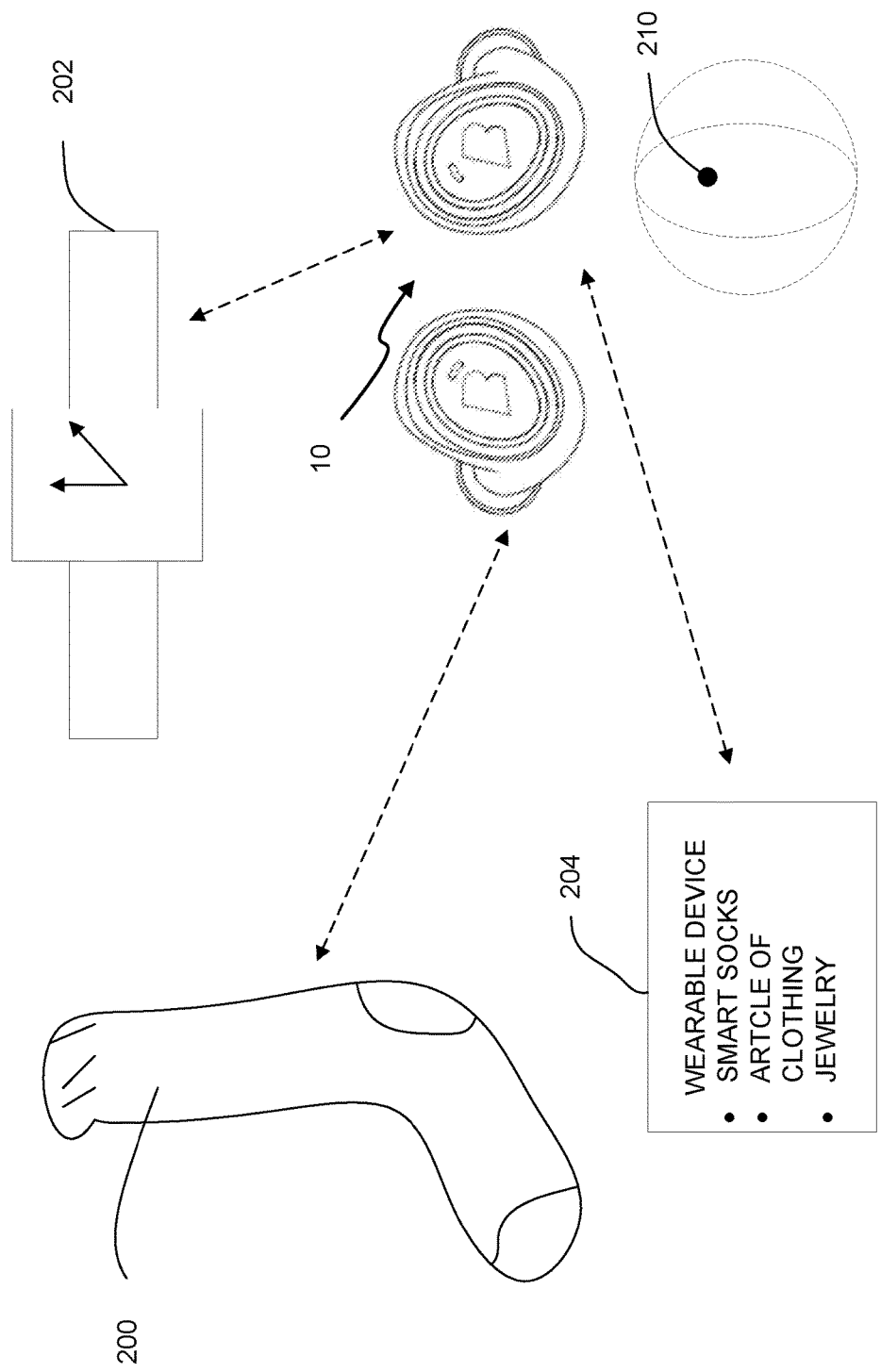
FIG. 5 illustrates a network of distributed sensors in operative communication with a set of wireless earpieces.

FIG. 5 illustrates a pictorial representation of a network of body sensors associated with body worn or wearable devices 204 which may include smart socks 200, articles of clothing, jewelry, watches with watch bands 202, fitness bands, or any other number of different body worn items. As shown in FIG. 5, the set of wireless earpieces 10 may communicate with each individual body sensor within the network of body sensors. The communication may be one-way or bi-directional depending upon the embodiment. This communication may take place in various ways. In one embodiment, audio may be generated at the body worn or wearable devices which is detected at the wireless earpieces 20. The audio may be outside a range of normal human hearing such as above 20 kHz. Alternatively, this communication may take place such as by communicating data through the skin such as by method disclosed in U.S. Pat. No. 6,754,472 to Williams et al., hereby incorporated by reference in its entirety. Where communication takes place through the skin each of the wearable devices may have contact areas for electrically connecting with the skin. In other embodiments, this communication may take place through radio communications. Where this communication takes place through radio communications, it is preferred that both a left earpiece and a right earpiece be used with each of the left earpiece and the right earpiece capable of communication with the wearable devices. Signal strength and other signal characteristics may be used to identify relative location of the wearable devices to the wireless earpieces. For example, a sock with a stronger signal strength with a left earpiece than a right earpiece may be indicative that the sock is being worn on a left foot instead of a right foot. Of course, direction finding, triangulation, and/or other techniques may be applied to locate particular body worn devices relative to one or more wireless earpieces.

The audiometric feedback produced may be in a three dimensional manner. Thus, different perceived sound sources 210 may be placed at different locations within a three-dimensional sound space as shown. Thus, for example, audiometric feedback may be perceived as being reproduced from particular locations. For example, audiometric feedback may be perceived as being reproduced from a location of the sensor for which the audiometric feedback is provided.

Therefore, various method, system and apparatus have been shown and described. Numerous options, variations, and alternatives are contemplated. The present invention is not to be limited to the specific embodiments shown and described herein.

What is claimed is:

1. A method of providing audiometric feedback from a network of distributed body sensors using one or more wireless earpieces comprising:
    receiving at least a first signal from a first individual body sensor within the network of distributed body sensors at the one or more wireless earpieces;
    receiving at least a second signal from a second individual body sensor within the network of distributed body sensors at the one or more wireless earpieces;
    processing at least the first signal and the second signal received at the one or more wireless earpieces by a processor of the one or more wireless earpieces to determine a location of the first individual body sensor and the second individual body sensor within the network of distributed body sensors relative to the one or more wireless earpieces;
    producing audiometric feedback at the one or more wireless earpieces at least partially based on the location of at least one of the first individual body sensor and the second individual body sensor relative to the one or more wireless earpieces.

2. The method of claim 1 wherein the signals are sound signals.

3. The method of claim 2 wherein the audiometric feedback is based on changes in the location of the individual body sensors relative to the one or more wireless earpieces due to movement.

4. The method of claim 3 wherein the audiometric feedback comprises an audiometric rhythmic signal synchronized to the movement.

5. The method of claim 4 further comprising encoding sensor information from the individual body sensors within the sound signals and decoding the sensor information from the individual body sensors at the one or more wireless earpieces.

6. The method of claim 1 wherein the signals are communicated over skin of a user of the distributed body sensors and the one or more wireless earpieces.

7. The method of claim 1 wherein at least one of the distributed body sensors is associated with an article of clothing.

8. The method of claim 1 wherein at least one of the distributed body sensors is associated with a band.

9. The method of claim 1 wherein the audiometric feedback is represented by three dimensional sound and wherein the one or more wireless earpieces comprises a left earpiece and a right earpiece.

10. The method of claim 9 wherein the audiometric feedback is positioned at a location so as to be perceived as emanating from a position of one of the individual body sensors.

11. The method of claim 1 wherein the signals are wireless signals.

12. A method of providing audiometric feedback from a network of distributed body sensors using one or more wireless earpieces comprising:
   receiving at least a first signal from a first individual body sensor within the network of distributed body sensors at the one or more wireless earpieces;
   receiving at least a second signal from a second individual body sensor within the network of distributed body sensors at the one or more wireless earpieces;
   wherein the first signal and the second signal are received by the one or more wireless earpieces at a different time or rate;
   processing at least the first signal and the second signal received at the one or more wireless earpieces to determine location of at least one of the first individual body sensor and the second individual body sensor within the network of distributed body sensors relative to the one or more wireless earpieces;
   producing audiometric feedback at the one or more wireless earpieces at least partially based on the location of at least one of the first individual body sensor and the second individual body sensor relative to the one or more wireless earpieces.

13. The method of claim 12 wherein the at least one wireless earpieces comprises a left earpiece and a right earpiece.

14. The method of claim 13 wherein the first signal is received at the left earpiece and has a first arrival time and a first angle of incidence and the second signal is received at the right earpiece and has a second arrival time and a second angle of incidence.

15. The method of claim 14 wherein a processor disposed within the left earpiece or the right earpiece determines the location of at least one of the individual body sensors using the first arrival time and the first angle of incidence and the second arrival time and the second angle of incidence.

16. The method of claim 13 wherein the audiometric feedback is perceived as emanating from a position of at least one of the individual body sensors.

17. The method of claim 12 wherein the one or more wireless earpieces is configured to triangulate the location of at least one of the individual body sensors.

18. The method of claim 12 wherein the one or more wireless earpieces further comprises at least one wireless transceiver configured to communicate with an external electronic device.

19. The method of claim 12 wherein the one or more wireless earpieces further comprises a plurality of microphones operatively connected to the wireless earpieces and a speaker is operatively connected to the one or more wireless earpieces.

20. The method of claim 19 wherein the location of at least one of the individual body sensors is determined by sound intensity differential.

* * * * *